(12) United States Patent
Braun et al.

(10) Patent No.: US 6,514,756 B1
(45) Date of Patent: Feb. 4, 2003

(54) HUMAN MYOBLAST CELL LINES AND THEIR USES

(75) Inventors: Serge Braun, Dorlisheim (FR); Frederic Perraud, Geudertheim (FR)

(73) Assignee: Transgene S.A., Strasbourg (FR)

( * ) Notice: Subject to any disclaimer, the term of this patent is extended or adjusted under 35 U.S.C. 154(b) by 0 days.

(21) Appl. No.: 09/559,781

(22) Filed: Apr. 27, 2000

Related U.S. Application Data
(60) Provisional application No. 60/186,761, filed on Mar. 3, 2000.

(30) Foreign Application Priority Data

Apr. 27, 1999 (EP) .............................................. 99401031

(51) Int. Cl.$^7$ .............................................. C12N 15/85
(52) U.S. Cl. ...................................................... 435/325
(58) Field of Search ............................... 435/325, 320.1

(56) References Cited

FOREIGN PATENT DOCUMENTS

| WO | WO 98/10058 | * | 3/1998 |
|---|---|---|---|

OTHER PUBLICATIONS

Krauer et al., Regulation of interleukin–1Beta transcription by epstein–barr virus involves a number of latent proteins via theit interaction with RBP, 1998, Virology, vol. 252, pp. 418–430.*

Walther et al., Viral vectors for gene transfer, 2000, Drugs, vol. 60, pp. 249–271.*

Simon et al., Establishment of long–term myogenic cultures from patients with duchenne muscular dystrophy by retroviral transduction of a temperature–sensitive SV40 large T antigen, 1996, Experimental Cell Research, vol. 224, pp. 264–271.*

Murahashi et al., Immortalization of human aortic smooth muscle cells with orgin–minus simian virus 40 DNA, 1992, Biotechnology and Applied Biochemistry, vol. 16, pp. 152–160.*

Nakamigawa et al., Generation of human myogenic cell lines by the transformation of primary culture with origin–defective SV40 DNA, 1988, Journal of Neurological Sciences, vol. 83, pp. 305–319.*

* cited by examiner

*Primary Examiner*—Remy Yucel
*Assistant Examiner*—Celine Qian
(74) *Attorney, Agent, or Firm*—Burns, Doane, Swecker & Mathis, L.L.P.

(57) ABSTRACT

Described is a human muscular cell line which is able to proliferate and generated from primary human muscular cells by a process comprising the step of:

Figure 1:
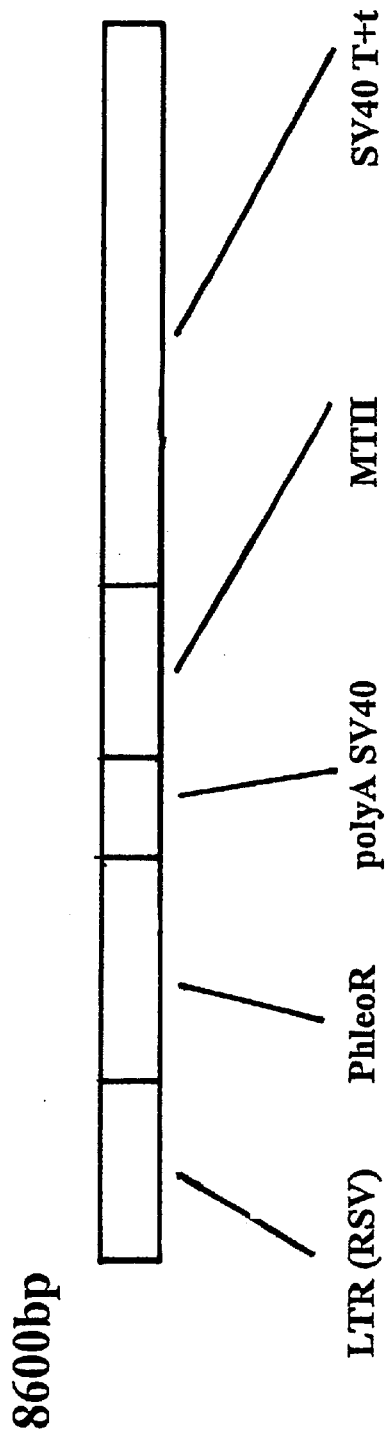

a) pre-treating a culture of said primary human muscular cells or a suspension thereof with at least one glucocorticoid, b) optional step comprising obtaining a suspension of said pre-treated culture of step a), c) transferring into the pre-treated cells of the suspension of step a) or b) at least one nucleic acid vector which is not of retroviral origin and which is competent to immortalize said pre-treated cells and d) culturing the transferred cells of step c).

Furthermore, human muscular cells derived from said cell lines are provided as well as pharmaceutical and diagnostic compositions comprising the same.

6 Claims, 1 Drawing Sheet

LTR: RSV, LTR promoter.
Phleo: Phleomycin resistance gene.
MTII: Mouse metallothionein II gene promoter.
SV40 t+T: Large T and Small t SV40 antigens coding regions.

HUMAN MYOBLAST CELL LINES AND THEIR USES

This application claims priority under 35 U.S.C. §§119 (e) to Provisional Application No. 60/186,761 filed in the United States on Mar, 3, 2000; the entire content of which is hereby incorporated by reference.

The present invention relates generally to the field of human muscular cell lines, and more particular to human myoblast cell lines produced by a new process and to uses of these cell lines, especially in gene therapy or in understanding and approach of the etiology of diseases affecting muscle tissue.

Cell lines are widely used as in vitro models for studying the events involved during in vivo cellular or tissular development. For example, muscular development events can be reproduced during the differentiation of muscle cell lines. Accordingly, permanent mammalian cell lines, especially human myogenic cell lines, would be of considerable value for providing useful tools for dissecting the molecular and biochemical cellular events, for identifying and testing new drugs for muscular diseases, such as dystrophies, for the study of myogenesis, etc . . . .

In vivo, myoblasts are precursor cells of the mesoderm that are destined for myogenesis. The determined myoblasts are capable of recognizing and spontaneously fusing with other myoblasts leading to the production of a differentiated myotube. The multinucleated myotube no longer divides nor synthesizes DNA, but it produces muscle proteins in large quantity which are constituents of the contractile apparatus and specialized cell-surface components essential to neuromuscular transmission.

Some myogenic spontaneous cell lines have been isolated from primary muscle cultures obtained by enzymatic disaggregation of rodent skeletal muscle (Mulle et al., 1988, P.N.A.S., USA, 85, 5728–5732). However, primary myogenic clones obtained from human muscle do not give rise to such cell lines and show a finite life span which diminishes with increasing donor age. Moreover, the proliferation capacity of myoblasts from patients with Duchenne muscular dystrophy (DMD) is particularly restricted in vitro (Webster et Blau, 1990, Som. Cell. Mol. Genet., 16, 557–565) preventing for obtaining a satisfactory testing or studying model for this disease.

Furthermore, there is substantial interest in developing ways in which myoblasts, produced as stable cell line, may be used for therapeutic purposes. For example, the myoblasts may serve as cell therapy vector for the treatment of various diseases associated with genetic or non-genetic defect, for vaccination protocols, involving muscle tissue as targeted tissue or administration site. In the specific case where myoblasts are used as carriers for gene therapy, one or more genes are introduced into said myoblasts which are selected among muscle or non-muscle genes and which encode a polypeptide useful for the treatment of muscle or non-muscle diseases, or for providing novel or enhanced genetic capabilities or new vaccination tool.

Moreover, it has been previously shown that in vivo the myoblasts are capable of migrating to distant sites, particularly to sites of injury, and of fusing into pre-existing fibers. In cellular gene therapy perspectives, this myoblast migration across basal lamina may allow with only a few administration of myoblasts serving as carriers for genes, to treat a relatively large area. Myoblasts may be administered by injecting directly into the damaged site or at adjacent tissue or may be introduced into the blood stream, particularly in a vessel feeding the-damaged site and upstream from such site.

In more widely therapeutic applications, the myoblasts may be used as non-modified cells or modified to express compounds of interest, to increase or decrease the expression or availability of surface membrane molecules, MHC antigens, etc . . . which may correct genetic defects, supply surface membrane proteins or secreted products such as immunogenic peptides at a site which may be located at a distant site of the administration site.

Nevertheless, the above described applications require first to establish cell lines in culture that are capable to proliferate, to differentiate and to express properties characteristic of the cells in the tissue from which they were derived. The ability to establish particular cell lines has been widely described for many, but not all, cell types. Some of them maintain their original characteristics although many lose their differentiated phenotype upon continuous passage in culture. Finally, unlike rat and mouse for which several cell lines exist, there are few or no established human muscular cell lines available for applications yet.

Fogel et Defendi, 1967, Proc. Nati. Acad. Sci., 58, 967–973, have demonstrated that human myoblasts were susceptible to infection with wild-type SV40 and that permanent cell lines could be generated following infection. However, these cell lines rapidly lost the ability to differentiate. Several immortalized myogenic cell lines have been isolated from primary muscle culture of rodent skeletal muscle (Yaffe, D. "Retention of differentiation potentialities during prolonged cultivation of myogenic cells" Proc Natl Acad Sci USA (1968) 61: 477–483 and Yaffe, D. and Saxel, O. "Serial passaging and differentiation of myogenic cells isolated from dystrophic mouse muscle" Nature (1977) 270: 725–727). However, clones obtained from human primary cultures do not give rise to spontaneous cell lines and have a finite life. This phenomenon could be related to the observation that muscle tumors are very rare. More recently, Simon et al, 1996, Exp. Cell Res., 224, 264–271 have for the first time obtained long-term myogenic cultures from DMD muscle by infection of explant cultures with a recombinant retrovirus containing a mutated, temperature-sensitive form of the SV40 large T oncogene. Nevertheless, use of retrovirus is not satisfactory in terms of safety because they are integrating virus, said integration could interfere with the expression of vital genes or result in viral protein expression which can lead to CTL response in the treated patient.

Accordingly, the prior art is deficient in providing a satisfactory human muscular cell lines which can proliferate and differentiate, especially originating from muscular biopsies obtained from Duchenne muscular dystrophy (DMD) patients as well as from normal, dystrophin-positive individuals. The present invention fulfills this longstanding need and desire in the art.

The present invention provides human muscular cell lines obtained according to an improved process for establishing long-term mammalian cell line. Said human muscular cell lines show a great proliferative capacity, are able to differentiate and may prove valuable for in vitro investigations related to the cellular and molecular muscular metabolisms, to new drug screening or to methods assessing for cellular toxicity or cellular damages and providing a cellular model of choice for studies aimed to correct the molecular pathology of diseases, especially inherited disorders such as DMD.

Thus, the present invention first concerns a human muscular cell line which is able to proliferate wherein said human muscular cell line is generated from primary human muscular cells by a process comprising the step of:

a) pre-treating a culture of said primary human muscular cells or a suspension thereof with at least one glucocorticoid, b) optional step comprising obtaining a suspension of said pre-treated culture of step a), c) transferring into the pre-treated cells of the suspension of step a) or b) at least one nucleic acid vector which is not of retroviral origin and which is competent to immortalize said pre-treated cells and d) culturing the transferred cells of step c).

In accordance with the present invention, immortalized human myogenic cell lines from skeletal muscle biopsies have been established using the calcium phosphate transfection with a SV40 large T Antigen (TAg) plasmid further carrying a phleomycine selection gene. After transfection and selection, clones were derived. They express TAg and the myoblast natural marker desmin. In appropriate culture conditions, cells of said cell lines aligned and fused to form multinucleated myotubes, indicating they still proliferate, differentiate and express properties characteristic of muscular cells. Thus, the present invention for the first time generated myogenic clones based on tranformation of primary cells isolated from healthy and Duchenne Muscular Dystrophy (DMD) patients with plasmid. Said cell lines are usefull for example in pharmacological screening of drug able to restore a dystrophin-like activity (i.e, Utrophin) in Duchenne myoblasts, or in applications such as engraftment of encapsulated cells. The implications of the findings of the invention will be explained in more detail below.

According to a first embodiment of the present invention, said process comprises the step of:

a) obtaining a culture of said primary human muscular cells, b) pre-treating the culture of step a) with at least one glucocorticoid, c) obtaining a suspension of said pre-treated culture of step b), d) transferring into the pre-treated cells of the suspension of step c) at least one nucleic acid vector which is not of retroviral origin and which is competent to immortalize said pre-treated cells and e) culturing the transferred cells of step d).

According to a second embodiment, said process comprises the step of:

a) obtaining a culture of said primary human muscular cells, b) obtaining a suspension of said cultured primary human muscular cells of step a), c) pre-treating the suspension of step b) with at least one glucocorticoid, d) transferring into the pre-treated cells of the suspension of step c) at least one nucleic acid vector which is not of retroviral origin and which is competent to immortalize said pre-treated cells and e) culturing the transferred cells of step d).

The cells generated in accordance with the invention preferably have specific properties with regard to their ability to proliferate, to differentiate and to express properties characteristic of muscular cells. These properties are well documented in the cell line generation field. The specific cells of the present invention are able to proliferate, to differentiate and to express properties characteristic of muscular cells for at least 40 days.

According to the present invention, the transferring step should preferably be performed on a cell suspension. Accordingly, in the special case where the cultured primary human muscular cells of step a) are not in the form of a suspension, the process should comprise a specific step consisting in obtaining a suspension of cultured primary human muscular cells or of pre-treated culture thereof.

According to a preferred embodiment, the cell suspension is extemporaneously prepared before the transferring step.

"Suspension of cells" means that the cells do not adhere to solid support.

Methods for preparing suspension of cells are disclosed in litterature and may comprises a treatment of primary human muscular cells culture or of human tissue by mechanical tools (scraping, crushing . . . ) or by chemical treatment with at least one compound capable of disaggregating cell organization, for example an enzyme selected from the group consisting of pancreatin, collagenase, dispase, trypsin, hyaluronidase, and equivalents thereof, with EDTA or by temperature variation (e.g., 4° C. treatment). Said compound or equivalent include all natural, modified or part of said compound or enzyme which is still capable of disaggregating cell organization and producing isolated cells which can easily be suspended. These mechanical or chemical treatments are widely used, have been reported in the literature (Tissue dissociation Guide, Worthington Biochemical Corporation) and can be readily obtained or adapted by those skilled in the art.

For example, muscular cell organization may be dissociated by successive treatments with trypsin, for example 0.05% trypsin—EDTA 37° C. in a trypsinization flask with constant stirring. The cells collected in the supernatent after each trypsin treatment are pooled and cooled to 4° C. on ice. Calf serum is added to a final concentration of 10% (vol/vol) to terminate further protease activity. The dissociated cells are then centrifuged and the cell pellet is resuspended in conditioned media and either plated in culture, frozen in liquid nitrogen or submitted to the process of the instant invention. According to a preferred embodiment, the primary muscular human cells of interest may be enriched to greater than 70%, preferably more than 90% and more preferably more than 99% purity by using a method of enrichment widely used in the art, such as cell purification using monoclonal antibodies or preplating methods based on adherence properties.

According to step a) of the process, a culture of primary human muscular cells is obtained. Cellular culture methods are widely used in the technical field of the present invention and the skilled man can easily select the media and growth conditions adapted to the initial primary human muscular cells sample used.

The invention is based on a specific step comprising a pre-treatement of the cultured primary human muscular cells, eventually in the form of a suspension, with at least one glucocorticoid. Generally, any glucocorticoid may be used in the process of the present invention. Representative examples of useful glucocorticoids include dexamethasone, betamethasone, budesonide, hydrocortisone, prednisone, prednisolone, triamcinolone and flunisolide. The glucocorticoid may be either in a lipid soluble form, an ethanol soluble form or a water soluble form, and may further be either a synthetic and a non-synthetic glucocorticoid.

The pre-treatment step consists more particularly in contacting said cultured primary human muscular cells or a suspension thereof with at least one glucocorticoid. This pre-treatment of primary human muscular cells may be applied at least 3 hours, preferably at least 24 hours, and more preferably at least 48 hours before the transferring step.

The glucocorticoid concentration in the cells pre-treatment step ranges from $10^{-4}$ M to $10^{-10}$ M. In the specific case where the glucocorticoid is dexamethasone or hydrocortisone, said glucocorticoid concentration should preferably be ranging near $10^{-6}$ M or $10^{-5}$ M, respectively.

Although the process of the invention should at least comprise a glucocorticoid pre-treatment of the cells before the transferring step, according to another embodiment, it is also possible to envisage the use of said glucocorticoid in the steps of obtaining a cell suspension or transferring the nucleic acid vector.

Another essential step of the process leading to generate human muscular cell line of the invention, comprises introducing into pre-treated cells a nucleic acid vector competent to immortalize said pre-treated cells.

"Nucleic acid sequence competent to immortalize cells" means that due to the expression of a nucleic acid sequence competent to immortalize cells, cells were capable of in vitro growth for at least 100 doublings, compared with the normal situation where senescence occurs after 30 doublings, they are considered to be immortal. Transforming oncogenes are for example those which produce foci of transformed cells in a monolayer of NIH3T3 cells.

Literature provides many examples of such nucleic acid sequences which are competent to immortalize cells (Katakura et al., 1998, Methods Cell Biol., 57, 69–91). According to a preferred embodiment, this nucleic acid vector comprises at least one nucleic acid sequence encoding an oncogenic polypeptide such as myc, SV40 T antigen, SV40 t antigen, papillomaviruses E6 and E7, polyoma Large T gene, EBV, ras, adenovirus E1, p53 or an oncogenic part of any one thereof.

In order to permit introduction and expression of said immortalizing nucleic acid sequence into targeted cell, it is incorporated into a nucleic acid vector comprising genetic elements necessary for the expression of said nucleic acid sequence into said cell.

According to the present invention, "nucleic acid vector" means a nucleic acid construct which may be either a DNA and/or RNA, single or double-stranded, linear or circular, natural or synthetic, modified or not (see U.S. Pat, No. 5,525,711; U.S. Pat. No. 4,711,955; U.S. Pat. No. 5,792,608 or EP-A-302,175 for modification examples) defining a fragment or a portion of a nucleic acid, without size limitation. It may be, inter alia, a genomic DNA, a cDNA, a mRNA, an antisense RNA, a ribozyme, or DNA encoding such RNAs. The "nucleic acid vector" may be in the form of linear nucleic acid construct, and preferably in the form of plasmid. According to the invention, said "nucleic acid vector" should preferably be understood as a naked nucleic acid construct (Wolff et al., Science 247 (1990), 1465–1468) or as nucleic acid construct formulated with at least one compound such as polypeptides, preferably viral polypeptides, or cationic lipids or cationic polymers which can participate in the uptake of the nucleic acid construct into the cells (see Ledley, Human Gene Therapy 6 (1995), 1129–1144 for a review). According to the present invention, the "nucleic acid vector" should preferrably contain at least one nucleic acid sequence competent to immortalize cells pre-treated according to the process of the invention. As this particular sequence encodes at least one polypeptide which is involved in cellular immortalization, said "nucleic acid vector" should further contain elements necessary for expression of said nucleic acid sequence. Transcriptional promoters suitable for use in various vertebrate systems are well known. For example, suitable promoters include viral promoters like RSV, MPSV, SV40, CMV or 7.5 k, vaccinia promoter, inducible promoters, metalothionein promoter, etc. According to a preferred embodiment, said elements necessary for the expression of the nucleic acid sequence are activable by glucocorticoid (Geley et al., 1996, Review of Physiology, Biochemistry and Pharmacology, 128, 1–97). The "nucleic acid vector" can further include intron sequences, targeting sequences, transport sequences, sequences involved in replication or integration or selective sequence encoding for example for antibiotic resistance (ampicilin, phleomycin, chloramphenicol, . . . ). Example of such sequences have been reported in the literature and can be readily obtained by those skilled in the art. The "nucleic acid vector" can also be modified in order to be stabilized with specific components such as spermine.

In a particular embodiment, the nucleic acid vector further comprises at least one second nucleic acid sequence encoding all or part of a therapeutic or prophylactic polypeptide. Examples of such polypeptides are enzymes, hormones, cytokines, membrane receptors, targetting polypeptide, structural polypeptides, transport polypeptides, tumoral, viral or infectious antigens, adhesines, albumin, ligands, transcription factors, transduction factors, replication factors, stabilization factors, antibodies, E6 or E7 from HPV, MUC1, BRCA1, interferons, interleukin (IL-2, IL-4, IL-6, IL-7, IL-12, GM-CSF (Granulocyte Macrophage Colony Stimulating Factor), the tk gene from Herpes Simplex type 1 virus (HSV-1)or VEGF. According to a preferred embodiment, said nucleic acid sequence encodes all or part of dystrophin. Furthermore, said DNA may encode all or part of a polypeptide which is an immunity conferring polypeptide and acts as endogenous immunogen to provoke a humoral or cellular response, or both, against infectious agents, including intracellular viruses, and also against tumor cells. An "immunity conferring polypeptide" means that said polypeptide when it is expressed can participate to an immune response into a treated patient. The polynucleotide can also code for an antibody. In this regard, antibody encompasses whole immunoglobin of any class, chimeric antibodies and hybrid antibodies with dual or multiple antigen or epitope specificities, and fragments, such as $F(ab)_2$, Fab', Fab including hybrid fragments and anti-idiotypes (U.S. Pat. No. 4,699,880).

According to the transferring step, the nucleic acid sequence, or more broadly the nucleic acid vector comprising said sequence, is transferred into pre-treated cell in suspension by any of a wide variety of ways, including method selected from the group consisting of adenoviral infection, transfection with nucleic acid coated particles such as lipoplexes (cationic lipid/nucleic acid complexes) or polyplexes (cationic polymer/nucleic acid complexes) or the like, calcium phosphate transfection of plasmid, transfection with naked nucleic acid, electroporation method or any combination therof. However, the particular method for introducing the foreign nucleic acid sequence is not crucial to the invention.

In a particular embodiment, the transferring step of the process is performed in presence of at least one glucocorticoid. The glucocorticoid used in said transferring step can be identical or different from the one used in cellular pre-treatment step.

Usually, the nucleic acid concentration in the transferring step will be selected to range from 0.1 to 100 $\mu g/10^6$ cells.

The primary human muscular cell treated according to the process described above can be a skeletal muscle cell, smooth muscle cell or cardiac cell. More specifically, said primary human muscular cell is a myoblast or a satellite cell. According to a preferred embodiment, the primary human muscular cell suspension which is cultured in step a) comprises at least muscular cells, and preferably myocytes, nevertheless, human muscular cell line can also be obtained by treating primary cell suspension incorporating non-muscular cells (i.e. fibroblasts, etc . . . ). In this special case, further selection can easily permit human muscular cell line selection.

The present invention also relates to a human muscular cell line generated as previously described by a specific treatment of primary human muscular cells, isolated from Duchenne Muscular Dystrophy patient or from non-Duchenne Muscular Dystrophy patient.

In a further preferred embodiment, the primary human muscular cells suspension contains myoblasts and the cell line produced are human myoblast cell lines.

Methods have been developed for production of myoblasts from fetal and adult tissue which can generate large volumes of myoblasts from adult tissue that are substantially free of other cells and which can be treated according to the present invention. Likewise, myoblast cells and methods of use are disclosed in the art (see for example WO93/03768, which cells may be grown in culture, purified from crude cell culture by cloning or with a flow cytometer (FACs) which also can be treated according to the present process. The myoblasts isolated from the cell lines generated according to the invention have the potential for being used in a variety of ways. First, the myoblasts may serve as cell therapy, either as wild type cells or genetically modified cells, for the treatment of various diseases associated with genetic or nongenetic defect involving muscle tissue. Said immortalized myoblasts may also be used as vehicles for gene therapy, where one or more genes may be introduced into the myoblasts to provide a product of interest. These gene may be muscle genes or non-muscle genes for the treatment of muscle or non-muscle diseases or for providing novel or enhanced genetic capabilities.

According to a particular embodiment, fibroblasts isolated from muscle tissue may be converted heritably to myoblasts that express muscle genes and have a muscle cytoarchitecture. This is achieved by expression of a gene encoding MyoD or myogenin or another member of this gene family for constitutive expression. Such genetically engineered "myoblasts" may serve in place of true myoblasts in all of the manipulations or process described in the present invention. According to the present invention, "myoblasts" also encompasses said genetically engineered "myoblasts".

The present invention is more specifically directed to a human myoblast cell line produced from primary muscular cell isolated from Duchenne Muscular Dystrophy patient and designated Myoh TGD24 CNCM N°I-2127 and to a human myoblast cell line produced from primary muscular cell isolated from non-Duchenne Muscular Dystrophy patient and designated Myoh TG1 CNCM N°I-2128.

The present invention further concerns a human muscular cell line as previously described which is further modified by introducing a second nucleic acid sequence encoding all or part of a therapeutic or prophylactic polypeptide. Said second nucleic acid sequence is as previously defined and preferably encodes all or part of dystrophin or immunity-conferring polypeptide.

The invention also provides human muscular cells isolated from human muscular cell line of the present invention.

The present invention further relates to a pharmaceutical composition comprising at least one human muscular cell isolated from human muscular cell line of the present invention. According to a preferred embodiment, said human muscular cell comprised in said pharmaceutical composition is encapsulated. Cell encapsulation methodology has been previously described which allows transplantation of encapsulated cells in treatment of Parkinson's disease (Tresco et al., 1992, ASAIO J. 38, 17–23) or Amyotrophic lateral sclerosis (Aebischer et al., 1996, Hum. Gene Ther. 7, 851–860). According to said specific embodiment, cells are encapsulated by compounds which form a microporous membrane, and said encapsulated cells can further be implanted in vivo. Capsules, for example approximately 1 cm in length containing the cells of interest may be prepared employing a hollow microporous membrane fabricated from poly-ether-sulfone (PES) (Akzo Nobel Faser AG, Wuppertal, Germany; Déglon et al, 1996, Hum. Gene Ther. 7, 2135–2146). This membrane has a molecular weight cutoff greater than 1,000,000 Da, which permits the free passage of proteins and nutrients between the capsule interior and exterior, while preventing the contact of transplanted cells with host cells. The entrapped cells may be implanted by intradermal, subdermal, intravenous, intramuscular, intranasal, intracerebral, intratracheal, intraarterial, intraperitoneal, intravesical, intrapleural, intracoronary or intratumoral ways.

In a further embodiment, the invention concerns the use of at least one human muscular cell generated, and eventually modified, as described above for the preparation of a composition for administration into a human tissue. In a preferred embodiment the prepared composition in accordance with the use claimed in the present invention is in a form for administration into a vertebrate tissue. These tissues include those of muscle, skin, nose, lung, liver, spleen, bone marrow, thymus, heart, lymph, bone, cartilage, pancreas, kidney, gall bladder, stomach, intestine, testis, ovary, uterus, rectum, nervous system, eye, gland, connective tissue, blood, tumor etc. The administration may be made by intradermal, subdermal, intravenous, intramuscular, intranasal, intracerebral, intratracheal, intraarterial, intraperitoneal, intravesical, intrapleural, intracoronary or intratumoral injection, with a syringe or other devices. Moreover, myoblast cells are found to migrate from the original site of administration to other sites, particularly injured sites, e.g. degenerating foci. This migration phenomenom permits the treatment of injured sites by injecting myoblasts into the patient in need, particularly in tissue, usually muscle tissue, proximal to the injuries, although injection into the circulation or at a distal site may also be possible. By employing genetically engineered myoblasts one may provide for directed application of products of interest to the injured region. Usually, cell injection will be about $10^4$ to $10^7$ cells (modified or not) per $cm^3$ of muscle tissue to be treated. In this particular case, the composition according to the invention may also comprise a pharmaceutically acceptable injectable carrier. The carrier is preferably isotonic, hypotonic or weakly hypertonic and has a relatively low ionic strength, such as provided by a sucrose solution. It includes any relevant solvent, aqueous or partly aqueous liquid carrier comprising sterile, pyrogen-free water, dispersion media, coatings, and/or equivalents. The pH of the pharmaceutical preparation is suitably adjusted and buffered.

In a further aspect, the invention relates to a diagnostic kit comprising at least one human muscular cell generated according to the invention useful for in vitro assessment of muscular cellular toxicity or damages of candidate or commercially available pharmaceutical molecules (pre-clinical assays) or for in vitro screening of new drugs. In course of said applications, cell lines generated from Duchenne Muscular Dystrophy patient would be preferred. The cell lines may also serve as a tool to analyse physiopathology of muscular diseases.

While the present invention has been described with reference to preferred embodiments and specific examples, one of the ordinary skill after reading the foregoing specification will be able to effect various changes, substitutions of equivalents, and other alterations to the processes and produced cells set forth herein. It is therefore intended that the protection claimed hereon be limited only by the definition contained in the appended claims and equivalents thereof.

EXAMPLES

Establishement of Human Myogenic Cell Lines from (i) a Healthy Donor and (ii) a Patient with Duchenne Muscular Dystrophy by the Process of the Present Invention 1. Materials The plasmid DNA (pPHMT—FIG. 1) used in the transferring step contains T and t antigenes coding regions from SV40 placed under the control of the mouse metallothionein II promoter. Selection gene is the procaryotic phleomycin resistance gene controlled by the LTR promoter from RSV.

2. Process of the Invention a) Culture of Primary Human Muscular Cells.

Myoblasts were obtained from muscles biopsies of a metabolically healthy patient after orthopedic surgery or from a DMD patient. Cells are harvested from explant cultures and grown in Ham's F14 medium (Life Technologies) supplemented with 10% fetal calf serum (Hyclone, Logan, Utah), 10 g/ml insulin, 10 ng/ml epidermal growth factor (both from Sigma), 10 ng/ml basic fibroblast growth factor (Pepro Tech, Rocky Hill, N.J.), 2 mM glutamine (bioMerieux, Marcy l'Etoile, France) and 40 g/ml gentamycin (Schering Plough, Kenilworth, N.J.). The process is performed on myoblasts obtained after a maximum of 12 passages and seeded (3000 cells/cm5) on 0.1% gelatin-coated dishes (100 mm diameter). Muscle cells are characterized by immunocytochemistry for desmin, dystrophin (NCL anti-human dystrophin monoclonal antibodies, Novocastra) and their ability to fuse and to form myotubes. Proportion of myoblasts in the culture used for the next step of the process is between 70 and 90%.

b) Pre-treatement of the Culture with Dexamethasone.

Two days before transfection step, $5.10E5$ cells are seeded in 100 mm diameter culture dishes in culture medium supplemented with $10^{-6}$ M dexamethasone (Sigma) diluted in ethanol.

c) Preparation of a Suspension of the Pre-treated Culture.

The pre-treated cell culture is submitted to a trypsination step using a 0.25% trypsin preparation. The culture medium is removed and the monolayer cells are rapidly rinced with few ml of trypsin preparation (Gibco). 0.5 ml of pre-warmed (37° C.) trypsin preparation is added. Trypsinisation step is performed for about 5 minutes at 37° C. and is monitored by inverted microscope observation of the monolayer cells. The cells from all dishes are collected by centrifugation and resuspended in 20 ml of dexamethasone containing culture medium, mecanically disrupted to complete the trypsinisation step and distributed in two sterile tubes.

d) Calcium Phosphate Transfection Step.

1 ml of calcium phosphate precipitate (20 μg DNA/ml)is added in each tube and a 100 mm culture dish is seeded with 11 ml of the transfection mixture (cells +precipitated plasmid DNA) for about 24 hours at 37 ° C., 5% CO2.

The transfected cells are then cultured in culture medium according to conventional culture method. The transfected clones are selected by adding phleomycin at 50 g/ml after 24 h. Dexamethasone is also added at each changement of culture medium until clones selection. The clone selection is performed by immunofluorescence staining.

According to this selection method, the transfected cells are cultured in Lab-Tek chamber slides (Nunc, Naperville, Ill., USA) for 2 days and fixed with methanol-acetone (1:1) for 10 min at –20 C. Slides are then incubated with anti-SV40 T antigen mouse monoclonal antibody (PAB-419; Chemicone) for 1 hour at room temperature, rinced with PBS buffer and rabbit anti-mouse IgG FITC-conjugated antibodies (ICN ImmunoBiologicals, Lisle, Ill., USA) is subsequently applied for 1 h at room temperature. Slides are mounted with a solution of Mowiol and examined under an epifluorescence microscope (Nikon).

3. Results

For human myoblasts a major problem is the refractoriness of those cells (healthy as well as DMD) to transfection. The transfection efficacy is very low when classical transfection techniques are used (around $10^7$). It could now be demonstrated in accordance with the present invention that the combination of a glucocorticoid pre-treatment of the target cells together with transfection step made on suspended cells allows the generation of immortalized clones (efficiency $10^{-5}$). For human DMD myoblasts, more than 15 clones were obtained, 3 of which were selected with regard to their ability to form myotubes. Moreover, it was observed that in order to preserve a good proliferating rate, the clones should preferably be plated at about 30% confluency. The isolated clones are preferably cultured in DMEM basal medium, 20%SVF, Insulin, EGF, bFGF, Dexamethasone and Zinc Sulfate.

Immunofluorescence study of clones demonstrated expression of SV40 TAg in all cells. The myoblasts natural marker "desmin" was also present, and some of the clones were able to fuse.

| Species | Number of clones obtained | Number of clones expressing TAg | Number of clones expressing Desmin | Number of fusing clones |
|---|---|---|---|---|
| Mdx | 19 | 19 | 3 | 0 |
| DMD | 33 | 33 | 10 | 3 |
| Healthy human | 21 | 20 | 5 | 4 |

Transfectability of the isolated cell lines has also been tested by calcium phosphate transfection using a plasmid expressing the Beta-Galactosidase gene (Beta-Gal).

Two of the identified clones were efficiently transfected: the clone MyohTG1 (healthy) (CNCM N° I-2128) and MyohTGD24 (Duchenne) (CNCM N°I-2127) which shown 1 to 10% of Beta-Gal expressing cells after transient transfection. These two clones are able to proliferate, to differentiate and to express properties characteristic of muscular cells and further can efficiently transfected with nucleic acid vector usefull for expressing gene of interest into said cells.

The clones Myoh TG1 and Myoh TGD24 have been deposited on Feb. 16, 1999 with the Collection Nationale de Cultures de Microorganimes (CNCM), Institut Pasteur, 25, Rue du Docteur Roux, F-75724 Paris Cedex 15 and have been attributed the CNCM accession no. I-2128 and I-2127, respectively.

What is claimed is:

1. A human myoblast cell line produced from primary muscle cells isolated from a Duchenne Muscular Dystrophy patient and designated Myoh TGD24 CNCM N°I-2127.

2. A human myoblast cell line produced from primary muscle cells isolated from a non-Duchenne Muscular Dystrophy patient and designated Myoh TG1 CNCM N°I-2128.

3. An isolated human myoblast cell from the human myoblast cell line of claim 1 or 2.

4. A pharmaceutical composition comprising an effective amount of at least one human myoblast cell from the human myoblast cell line of claim 2 and a pharmaceutically acceptable carrier therefor.

5. A pharmaceutical composition of claim 4 wherein said human myoblast cells are encapsulated.

6. An assay kit comprising at least one human myoblast cell of claim 3 useful for in vitro assessment of muscular cellular toxicity or damages of candidate molecules or for in vitro screw of new drugs.

* * * * *